United States Patent
Cortes

(10) Patent No.: US 10,858,320 B2
(45) Date of Patent: Dec. 8, 2020

(54) PROCESS FOR MANUFACTURING SUBSTITUTED 5-METHOXYMETHYLPYRIDINE-2,3-DICARBOXYLIC ACID DERIVATIVES

(71) Applicant: BASF AGROCHEMICAL PRODUCTS B.V., Manati, PR (US)

(72) Inventor: David Cortes, Quincy, IL (US)

(73) Assignee: BASF AGROCHEMICAL PRODUCTS B.V., Arnhem (NL)

( * ) Notice: Subject to any disclaimer, the term of this patent is extended or adjusted under 35 U.S.C. 154(b) by 0 days.

(21) Appl. No.: 15/410,214

(22) Filed: Jan. 19, 2017

(65) Prior Publication Data

US 2017/0226060 A1 Aug. 10, 2017

Related U.S. Application Data

(63) Continuation of application No. 13/133,008, filed as application No. PCT/EP2009/066496 on Dec. 7, 2009, now abandoned.

(60) Provisional application No. 61/120,613, filed on Dec. 8, 2008.

(51) Int. Cl.
*C07D 213/84* (2006.01)
*C07D 213/80* (2006.01)
*C07D 401/04* (2006.01)

(52) U.S. Cl.
CPC ......... *C07D 213/84* (2013.01); *C07D 213/80* (2013.01); *C07D 401/04* (2013.01)

(58) Field of Classification Search
CPC .................................................. C07D 213/08
See application file for complete search history.

(56) References Cited

U.S. PATENT DOCUMENTS

| | | | |
|---|---|---|---|
| 4,460,776 A | 7/1984 | Wepplo | |
| 5,177,266 A | 1/1993 | Strong | |
| 5,288,866 A | 2/1994 | Strong | |
| 5,378,843 A | 1/1995 | Strong | |
| 5,760,239 A | 6/1998 | Wu | |

FOREIGN PATENT DOCUMENTS

| | | |
|---|---|---|
| EP | 0 322 616 | 7/1989 |
| EP | 0 548 532 | 6/1993 |
| EP | 0 933 362 | 8/1999 |

OTHER PUBLICATIONS

Brecher "Graphical Representation Standards for Chemical Structure Diagrams" IUPAC, Pure and Applied Chemistry 80, 277-410, 2008.*
International Search Report prepared in International Application No. PCT/EP2009/066496, filed Dec. 7, 2009.
International Preliminary Report on Patentability from corresponding International Application No. PCT/EP2009/066496, filed Dec. 7, 2009.
Bi Q. et al., "Review on Synthesis of Imazamox", Modern Agrochemicals, (2007), pp. 11-12, 28, vol. 6, No. 2.
Watson, Will, "On Byproducts and Side Products", Org. Process Res. Dev., 2012, p. 1877, vol. 16.

* cited by examiner

*Primary Examiner* — David K O'Dell
(74) *Attorney, Agent, or Firm* — Marshall, Gerstein & Borun LLP

(57) ABSTRACT

A process for manufacturing a compound of formula (I), in a methanol/$H_2O$ mixture. Compounds of formula (I) are useful intermediates in the synthesis of herbicidal imidazolinones, like imazamox.

14 Claims, No Drawings

PROCESS FOR MANUFACTURING SUBSTITUTED 5-METHOXYMETHYLPYRIDINE-2,3-DICARBOXYLIC ACID DERIVATIVES

This application is a continuation of U.S. application Ser. No. 13/133,008, filed Jun. 6, 2011, the entire contents of which are hereby incorporated herein by reference. U.S. application Ser. No. 13/133,008, is a National Stage application of International Application No. PCT/EP2009/066496, filed Dec. 7, 2009, which claims the benefit of U.S. Provisional Application No. 61/120,613, filed Dec. 8, 2008, the entire contents of which are hereby incorporated herein by reference.

The invention relates to a process for manufacturing 5-methoxymethylpyridine-2,3-dicarboxylic acid derivatives and further conversion of these compounds to herbicidal 5-substituted-2-(2-imidazolin-2-yl) nicotinic acids, such as imazamox.

Derivatives of 2-(2-imidazolin-2-yl) nicotinic acids, like imazamox (2-[(RS)-4-isopropyl-4-methyl-5-oxo-2-imidazolin-2-yl]-5-methoxymethylnicotinic acid),

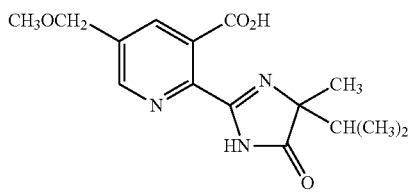

are useful selective herbicides which act as ALS-inhibitors and can be used in pre- and post-emergence applications.

Various processes for the synthesis of these compounds are known from the literature, see e.g. EP-A 0 322 616, U.S. Pat. Nos. 5,378,843, 5,760,239, EP-A 0 933 362 or Q. Bi et al, Modern Agrochemicals 6(2)(2007) 10-14.

U.S. Pat. No. 5,378,843 discloses the synthesis of 5-(methoxymethyl)-2,3-pyridinedicarboxylic acid by reaction of [(5,6-dicarboxy-3-pyridyl)methyl] trimethylammonium bromide di-methyl ester with sodium methoxide/methanol and NaOH/water, followed by acidification.

U.S. Pat. No. 5,760,239 discloses an improved method for the conversion of 5,6-dicarboxyl-3-pyridylmethyl ammonium halide to 5-(alkoxymethyl)pyridine-2,3-dicarboxylate salt via a single step closed reaction with the appropriate alcohol and a base at a temperature of about 120 to 180° C.

Although synthesis on an industrial scale is carried out by these methods there is still room for improvement, specifically in view of economical and ecological aspects, such as overall yield improvement or the avoidance of certain solvents or reagents.

One task of the invention is to provide an improved process for manufacturing 5-methoxymethylpyridine-2,3-dicarboxylic acids or carboxylates. A further task of the invention is to provide an improved process for converting these compounds to herbicidal 2-(2-imidazolin-2-yl) nicotinic acids or derivatives thereof.

It has been found that the methoxylation of 5,6-disubstituted-3-methylpyridines and further reaction with tertiary amines can be significantly improved by working in a system methanol/water and methanolate or a mixture of methanolate and hydroxide under pressure at a temperature of about 75 to 110° C.

Accordingly, in one aspect of the invention there is provided a process for manufacturing a 2,3-disubstituted-5-methoxymethylpyridine of formula (I),

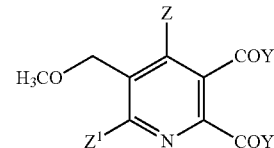

(I)

where
Z is H or halogen;
$Z^1$ is H, halogen, CN or $NO_2$;
Y is OM, and
M is H, an alkali metal or an alkaline earth metal,
comprising the step of:
(i) reacting a compound of formula (II)

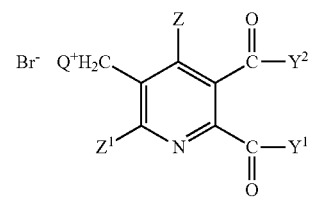

(II)

where
Q is a tertiary aliphatic or cyclic, saturated, partially unsaturated or aromatic amine;
Z is H or halogen;
$Z^1$ is H, halogen, CN or $NO_2$;
$Y^1$ and $Y^2$ are each independently $OR^1$, $NR^1R^2$, or when taken together $Y^1Y^2$ is —O—, —S— or —$NR^3$—;
$R^1$ and $R^2$ are each independently H, $C_1$-$C_4$ alkyl optionally substituted with $C_1$-$C_4$ alkoxy or phenyl optionally substituted with one to three $C_1$-$C_4$ alkyl groups, $C_1$-$C_4$ alkoxy groups or halogen atoms, or phenyl optionally substituted with one to three $C_1$-$C_4$ alkyl groups, $C_1$-$C_4$ alkoxy groups or halogen atoms;
$R^3$ is H or $C_1$-$C_4$ alkyl,
in a methanol/$H_2O$ mixture, comprising at least 20% by weight $H_2O$ (based on the sum of water and bromide (II)), with a base comprising $MOCH_3$ and/or MOH, where M is alkali metal or alkaline earth metal, under pressure in a closed vessel at a temperature of from about 75 to 110° C.

In a further aspect of the invention there is provided a process for preparing a herbicidal imidazolinone compound of formula (III),

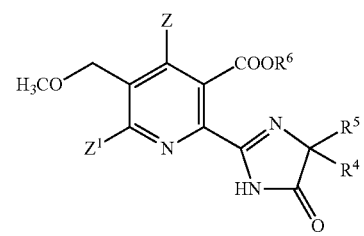

(III)

wherein

Z, $Z^1$ are as defined in formula (I);

$R^4$ is $C_1$-$C_4$ alkyl;

$R^5$ is $C_1$-$C_4$ alkyl, $C_3$-$C_6$ cycloalkyl or $R^4$ and $R^5$, when taken together with the atom to which they are attached, represent a $C_3$-$C_6$ cycloalkyl group optionally substituted with methyl, and $R^6$ is hydrogen; a group of the formula —N=C (lower alkyl)$_2$; $C_1$-$C_{12}$ alkyl optionally substituted with one of the following groups: $C_1$-$C_3$ alkoxy, halogen, hydroxyl, $C_3$-$C_6$-cycloalkyl, benzyloxy, fury, phenyl, halophenyl, lower alkyl-phenyl, lower alkoxyphenyl, nitrophenyl, carboxyl, lower alkoxycarbonyl, cyano or tri lower alkylammonium; $C_3$-$C_{12}$ alkenyl optionally substituted with one of the following groups: $C_1$-$C_3$ alkoxy, phenyl, halogen or lower alkoxy-cycloalkyl carbonyl or with two $C_1$-$C_3$ alkoxy groups or two halogen groups; $C_3$-$C_6$-optionally substituted with one or two $C_1$-$C_3$ alkyl groups; or a cation preferably selected from the group consisting of alkali metals, alkaline earth metals, manganese, copper, iron, zinc, cobalt, lead, silver, nickel, ammonium and organic ammonium;

comprising the steps of:

(i) preparing a compound of formula (I) as described above, (ii) converting the compound of formula (I) into the herbicidal compound of formula (III).

The process of the invention leads to higher yields, higher productivity (higher space time yields, lower fixed costs), lower raw material costs (NaOH is cheaper than Na-methylate) and an improved selectivity for the compounds of formula (I). It allows for lower temperatures, higher water contents and shorter reaction times.

Preferred are compounds of formula (I) where the symbols have the following meanings:

Z is preferably H.

$Z^1$ is preferably H.

Y is preferably OH.

Preferably, all symbols in formula (I) have the preferred meanings.

A particularly preferred compound of formula (I) is the compound of formula (Ia):

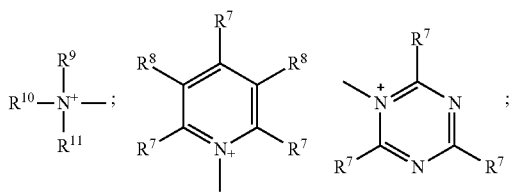

(Ia)

The compounds of formula (II) and their preparation are known, e.g. from U.S. Pat. No. 5,378,843.

Preferred compounds of formula (II) are the ones leading to the preferred compounds of formula (I). Preferably $Y^1$, $Y^2$ are $OR^1$ with $R^1$ being $C_1$-$C_4$ alkyl. It is understood that due to the presence of water partial hydrolysis of the diester (or other groups) may take place.

Q is preferably

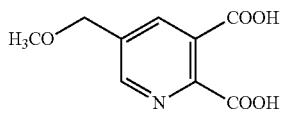

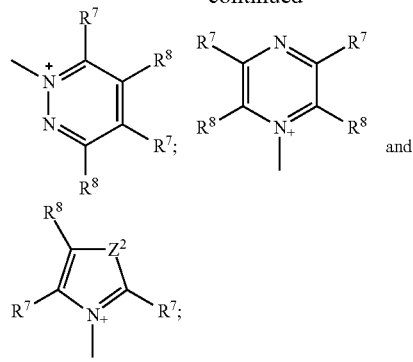

and

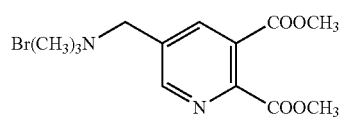

$Z^2$ is O, S or $NR^{12}$;

$R^{12}$ is $C_1$-$C_4$ alkyl;

$R^7$ and $R^8$ are each independently hydrogen, halogen, $C_1$-$C_4$ alkyl or $C_1$-$C_4$ alkoxy, or, when taken together, $R^7$ and $R^8$ form a 5- or 6-membered saturated or unsaturated ring optionally interrupted by O, S, or $NR^{12}$ and optionally substituted with one to three halogen atoms, $C_1$-$C_4$ alkyl groups or $C_1$-$C_4$ alkoxy groups, and $R^9$, $R^{10}$ and $R^{11}$ are each independently $C_1$-$C_4$ alkyl, or $R^9$ and $R^{10}$, when taken together, form a 5-or 6-membered ring in which $R^9R^{10}$, is represented by the structure: —$(CH_2)_n$—, optionally interrupted by O, S or $NR^9$, where n is an integer of 3, 4 or 5, provided $R^{11}$ is $C_1$-$C_4$ alkyl.

$Q^+$ is more preferably $^\oplus NR^9R^{10}R^{11}$ or pyridinium, and $R^9$, $R^{10}$ and $R^{11}$ are more preferably each independently $C_1$-$C_4$ alkyl, or $R^9$ and $R^{10}$, when taken together, form a 5-or 6-membered ring in which $R^9R^{10}$, is represented by the structure: —$(CH_2)_n$—, optionally interrupted by O, S or $NR^{12}$, where n is an integer or 3, 4 or 5, provided $R^{11}$ is $C_1$-$C_4$ alkyl; in particular preferably $R^9$, $R^{10}$ and $R^{11}$ are $C_1$-$C_4$ alkyl.

A particularly preferred compound of formula (II) is the compound of formula (IIa):

(IIa)

The reaction is carried out in a solvent mixture comprising methanol and at least 20% by weight of water (based on the sum of water and bromide (II)). Preferably the amount of water is from about 25 to about 75%, more preferably 30 to 70%, in particular from about 40 to about 50%. The remainder of the solvent mixture is methanol and up to about 50%, preferably up to about 20% of further solvents, preferably selected from toluene, chlorobenzene and ethanol.

The weight ratio of methanol to bromide (II) is generally in the range of from 0.5-25:1, preferably 1-20:1, more preferred 1-10:1, in particular 2-3:1.

The base comprises MeOM, MOH or a mixture of MeOM and MOH where M is alkali metal or alkaline earth metal, preferably Na or K, in particular Na. In cases of mixtures MeOM/MOH M can be the same or different, preferably it is the same.

If MeOM is present, the molar ratio of MeOM, preferably MeONNa, to bromide (II) is generally in the range of 1-10:1, preferably 1-7.5:1, more preferably 1.25-7:1, in particular 1.25-2:1.

If MOH is present, the molar ratio of MOH, preferably NaOH, to bromide (II) is generally in the range of 0.5-10:1, preferably 1-7:1, more preferably 3-5:1. If a mixture of MeOM and MOH is used as base the molar ratio of MOH to bromide (II) is generally in the range of 0.5-7.5:1, preferably 1-5:1, more preferably 3-5:1. In one preferred embodiment no MOH is added to the reaction mixture. For economical reasons it is advantageous to use an excess of MOH with respect to MeOM. In another preferred embodiment, only MOH is used in a ratio of 3-10:1, more preferred 4-7:1, more preferred 4.5-6:1.

The molar ratio of total base added/bromide (II) is generally from about 2.5-10:1, preferably from about 3-7:1, particularly preferred from about 4.5-6:1. MeOM is typically added dissolved in methanol. MOH is typically added dissolved in water.

The reaction is carried out at a temperature in the range of from about 75 to 110° C., preferably in the range of from about 80 to 105° C., more preferably in the range of from about 80 to 100° C.

The reaction is carried out in a closed vessel, e.g. in a Parr pressure reactor, at an elevated pressure which is generally in the range of from about 1.01 to 5.00 bar, preferably of from about 1.02 to 4.00 bar, in particular of from about 1.03 to 3.50 bar. In a preferred embodiment no external pressure is applied, and the reaction is carried out at the pressure building up from the solvents at the reaction temperature in the closed vessel.

The reaction time is generally in the range of from about 5 to 20 h, preferably in the range of from about 6 to 9 h, in particular about 8 h.

In a preferred embodiment bromide (II), containing from about 25 to 75% by weight water (based on the sum of water and bromide (II)), is taken up in methanol, aqueous NaOH is slowly added at a temperature in the range of from about 25 to 40° C., followed by NaOCH$_3$ in methanol which is slowly added at a temperature in the range of from about 40 to 50° C. The reaction mixture is then heated to the reaction temperature (typically 80 to 100° C.) in a pressure reactor, which is closed, whereupon pressure builds up as the reaction temperature is reached.

After completion of the reaction the mixture is cooled down and can be worked up according to known procedures, e.g. by cooling, treatment with an acid, such as sulfuric acid, until compound (I) precipitates and can be filtered off.

In a preferred embodiment of the invention there is provided a process for manufacturing compounds of formula (I), comprising the steps of
(i-1) reacting a compound of formula (IV),

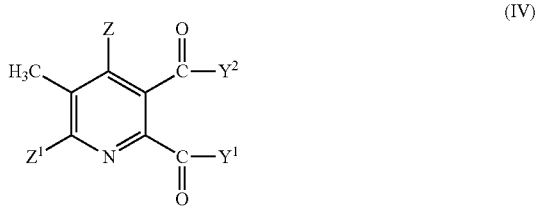

(IV)

wherein the symbols have the meaning given in formula (II), except that Y$^1$, Y$^2$ are not OH, with bromine in the presence of a radical initiator in a solvent mixture comprising an aqueous phase and an organic phase, where the organic phase comprises a solvent selected from 1,2-dichloroethane, chlorobenzene, 1,2-dichlorobenzene, 1,3-dichlorobenzene, 1,4-dichlorobenzene and tetrachloromethane, and where the pH-value of the aqueous phase is from 3 to <8, to obtain a 3-bromomethyl-5,6-disubstituted pyridine compound (V),

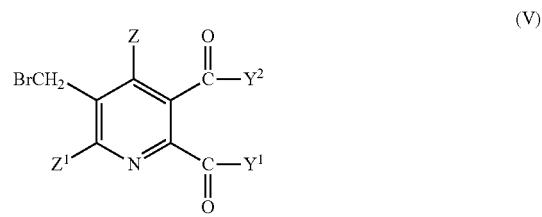

(V)

wherein Y$^1$, Y$^2$, Z and Z$^1$ have the meanings given in formula (II), except that Y$^1$, Y$^2$ are not OH, and
(i-2) reacting the bromo compound of formula (V) with a tertiary amine Q in a solvent at a temperature range of about 0 to 100° C. to obtain ammonium salt (II), and
(i-3) reacting ammonium salt (II) in a methanol/H$_2$O mixture, comprising with a base comprising MOCH$_3$ and MOH, where M is alkali metal, under pressure in a closed vessel at a temperature of from about 75 to 110° C.

In step (i-1) the molar ratio of pyridine compound (IV) to bromine is generally in the range of 1:0.5-1.2, preferably 1:0.6-1.0, more preferably 1:0.7-0.95.

It is also possible to work with half the equivalents of bromine, and to generate bromine in the reaction mixture from HBr with an oxidation agent like H$_2$O$_2$.

Suitable free-radical generators for initiating the reaction are those which decompose at the selected reaction temperature. Examples of preferred initiators are free-radical generators, such as azo compounds and peroxides. It is also possible, however, to use redox systems, especially those based on hydroperoxides, such as cumene hydroperoxide.

Radical initiators suitable for use in the method of the invention include 2,2'-azobisisobutyronitrile, 2,2'-azobis(2-methylbutanenitrile), 2,2'-azobis(2,4-dimethyl-pentanenitrile), 1,1'-azobis(cyclohexanecarbonitrile), organic and inorganic peroxides such as dilauroyl peroxide hydrogen peroxide, tert-butylperoxy-pivalate, benzoyl peroxide and the like, with 2,2'-azobisisobutyronitrile, 2,2'-azobis(2-methylbutanenitrile) and dilauroyl peroxide being preferred, and with 2,2'-azobisisobutyronitrile and 2,2'-azobis (2-methylbutanenitrile) being particularly preferred.

The molar ratio of initiator to bromine is preferably in the range of 0.04-0.15:1, more preferably 0.06-0.10:1.

The organic solvent is selected from the group consisting of 1,2-dichloroethane, chlorobenzene 1,2-dichlorobenzene, 1,3-dichlorobenzene, 1,4-dichlorobenzene and tetrachloromethane, preferably 1,2-dichloroethane and chlorobenzene. 1,2-dichloroethane is particularly preferred. Mixtures, in particular of the dichlorobenzenes, are also possible.

The amount of organic solvent may vary to a large extent. Preferably 900 to 2000 g, more preferably 1000 to 1300 g, organic solvent per mol of compound (II) are employed.

The reaction mixture comprises an organic phase and an aqueous phase. The amount of the aqueous phase may vary to a large extent. Preferably 140 to 500 g, more preferably 140 to 300 g, particularly 150 to 200 g of water per mol of the compound of formula (II) are employed.

During the course of the reaction the pH-value of the aqueous phase is kept in the range of from 3 to <8, preferably of from 3 to 7, more preferably of from 4 to 7. Control of the pH-value can be achieved by adding a suitable base, preferably an inorganic base such as a hydroxide of an alkali metal, e.g. NaOH, or an alkaline earth metal. Aqueous NaOH is a preferred base, particularly in diluted form (e.g. containing 5-20 wt.-% NaOH).

To achieve the desired control of the pH-value the base may be added continuously over the course of the reaction, or the pH-value is checked continuously and base is added by a connected automated dosage device.

In one preferred embodiment step (i-1) of the reaction is carried out by dissolving the compound (IV) in the organic phase and adding water to form the aqueous phase.

The initiator is added as pure compound or in solution, at room temperature or at reaction temperature after heating. Depending on the initiator decomposition temperature, a part or even the full amount of the initiator have to be added before the start of the bromine dosage. The amount of starter that has to be added during the bromine addition is also depending on the decomposition temperature. A minimum concentration of free radicals should be always available during the bromination reaction.

For 2,2'-azobis(2-methylbutanenitrile) a solution with initiator in an organic solvent is added. Slow addition of bromine as well as the base to control the pH-value can be started at the same time or some time later. It is preferred to start the bromine/base dosage later in order to have a sufficient amount of free radicals in the mixture when the bromination reaction starts. After completion of the reaction the mixture is cooled and the phases are separated.

The reaction is generally carried out at a temperature of about 50 to about 120° C., preferably about 60 to about 90° C.

The reaction may be carried out under atmospheric pressure or under excess pressure of up to 6 bar. Atmospheric pressure is preferred.

The reaction time (for step (i-1)) differs with the reaction parameters but is generally between 1 and 24 h.

In order to improve overall yield and enhance selectivity of the reaction, i.e. to reduce formation of the undesired dibromo and tribromo byproducts, it is preferred to carry out the reaction only up to a conversion of 5 to 60% (based on the amount of compound (IV)), preferably 30 to 55%. In one preferred embodiment the reaction is carried out up to a conversion of about 50% (based on compound (IV)). The degree of conversion may be checked by standard methods known to those skilled in the art, e.g. by HPLC analysis.

When the desired degree of conversion is reached the reaction is stopped and the phases are separated.

The organic phase, containing the product of step (i-1), compound (V), unreacted starting material (IV) and the dibromo and tribromo byproducts, may be extracted with water to remove water soluble impurities like acids and bromide. Product (III) can be isolated by known procedures, it is preferred, however, to use the organic phase without further work-up for the reaction with the tertiary amine Q (step (i-2)).

It is also possible to extract the aqueous phase with the organic solvent and to combine the organic phases in order to increase the yield of compound (V).

In step (i-2) of the reaction compound (V) is reacted with a tertiary amine Q to obtain the ammonium compound (II).

Preferred tertiary amines Q follow from the preferred meanings of Q in formula (II) above, i.e., pyridine and tertiary alkyl amines $NR^9R^{10}R^{11}$ are more preferred, where $R^9$, $R^{10}$ and $R^{11}$ are each independently $C_1$-$C_4$ alkyl, or, $R^9$ and $R^{10}$, when taken together, form a 5-or 6-membered ring in which $R^9R^{10}$ is represented by the structure: $-(CH_2)_n-$, optionally interrupted by O, S or $NR^{12}$, where n is an integer of 3, 4, or 5, provided $R^{11}$ is $C_1$-$C_4$ alkyl, and $R^{12}$ is $C_1$-$C_4$ alkyl.

Trimethylamine, $NMe_3$, is particularly preferred.

Generally an excess of tertiary amine is used. Typically 1.1 to 2, preferably 1.05 to 1.5 equivalents of tertiary amine per equivalent of compound (V) are employed.

Generally the tertiary amine, optionally dissolved in a solvent, is slowly added to the solution of compound (V), whereupon the salt (II) forms and precipitates. In case of the preferred amine $NMe_3$, which is gaseous at room temperature, it is preferred to work in a closed vessel and charge the gaseous amine or the liquidified amine under pressure to the solution of compound (V).

Step (i-2) is preferably carried out at a temperature of about 0 to 70° C., more preferably 5 to 70° C., particularly preferred 5 to 40° C. The reaction can be carried out at ambient pressure or at elevated pressure. In a preferred embodiment, the reaction is carried out in a closed vessel at the pressure of the solvent and/or amine building up at the reaction temperature.

Work up of the reaction mixture and isolation of the ammonium compound (II) can be carried out by conventional methods, e.g. compound (II) can be filtered off.

In a preferred embodiment water is added to the reaction mixture to dissolve the product, compound (II), and aqueous phase and organic phase are separated. The water phase may be further extracted with organic solvent in order to increase the purity of the product (II), and to increase the yield of recovered starting material (V) in the organic phase. The amount of water must be sufficient to form an aqueous phase and is preferably chosen to form a 20 to 45% by weight solution of compound (II) in the aqueous phase.

Ammonium compound (II) can be isolated from the aqueous phase by known methods. In a preferred embodiment compound (II) is not isolated and the aqueous phase obtained from step (i-2) is used in subsequent reactions without further workup. This is possible and advantageous, since a large amount of water is tolerated in the methoxylation process of the invention. However, it is also possible to mix the aqueous phase with a solvent that forms an azeotrope with water, e.g. toluene, and water is removed by azeotropic distillation. The resulting suspension of compound (II) can be used for further reactions.

In a further preferred embodiment, after separation of compound (V), the organic phase from step (i-2) containing up to 80% of starting material (IV) (based on the original amount used in step (i-1)) is recovered and recycled in the reaction process of step (i-1). Preferably further starting material (IV) is added to compensate for the amount converted in previous step (i-1). Thus, in principle, the organic phase of step (i-1) can be recycled any amount of times, however, due to an accumulation of byproducts, mainly the di- and tribromination product of compound (IV), up to 20, preferably up to 10 cycles are generally feasible.

In a preferred embodiment of the cyclic reaction process no additional starting material (IV) is added in the last cycle to improve the overall yield and conversion rate.

In a further embodiment of the cyclic reaction process a certain amount of the organic phase, preferably about 5 to 20% by weight, are removed to reduce or suppress accumulation of byproducts in the organic phase. In this embodiment of the invention there is virtually no limit to the number of cycles in which the organic phase can be used.

The compounds of formula (I) are valuable intermediates in organic synthesis. They are especially useful for conversion to herbicidal imidazolinone compounds (III).

Further conversion of compound (I) to herbicidal imidazolinones (III) can be achieved by methods known in the art.

Methods that may be used to create the imidazolinone herbicides are illustrated in the book "The Imidazolinone Herbicides" edited by D. L. Shaner and S. L. O'Connor, published 1991 by CRC Press, Boca Raton, Fla. with particular reference to Chapter 2 entitled "Synthesis of The Imidazolinone Herbicides", pages 8-14 and the references cited therein. The following patent literature references also illustrate the methods that may be used to convert the pyridine diacids, esters and salts to the imidazolinone final products:

U.S. Pat. Nos. 5,371,229; 5,250,694; 5,276,157; 5,110,930; 5,122,608; 5,206,368; 4,925,944; 4,921,961; 4,959,476; 5,103,009; 4,816,588; 4,757,146; 4,798,619; 4,766,218; 5,001,254; 5,021,078; 4,723,011; 4,709,036; 4,658,030; 4,608,079; 4,719,303; 4,562,257; 4,518,780; 4,474,962; 4,623,726; 4,750,978; 4,638,068; 4,439,607; 4,459,408; 4,459,409; 4,460,776; 4,125,727 and 4,758,667, and EP-A 0 041 623.

According to preferred embodiments of the invention conversion of compound (I) to a herbicidal imidazolinone (III) is carried out in analogy to the methods described in EP-A 0 041 623, U.S. Pat. No. 4,518,780 or EP-A 0 144 595.

According to these embodiments compound (I) is first converted to the respective anhydride by known methods, such as reaction with acetic anhydride.

In one embodiment compound (III) is prepared by
(i) preparation of a compound (I), where Y is OH, as outlined above;
(ii-1) conversion of compound (I) to the anhydride (VI),

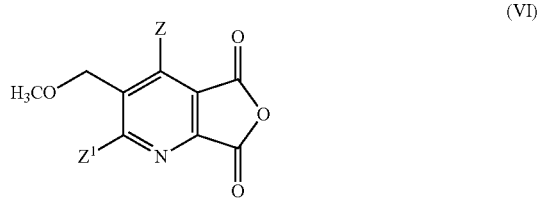
(VI)

(ii-2) reacting anhydride (VI) with an 2-aminoalkane carboxamide of formula (VII),

H$_2$N—CR$^4$R$^5$—CONH$_2$ (VII), where R$^4$ and R$^5$ are as in formula (III), to yield amide (VIII),

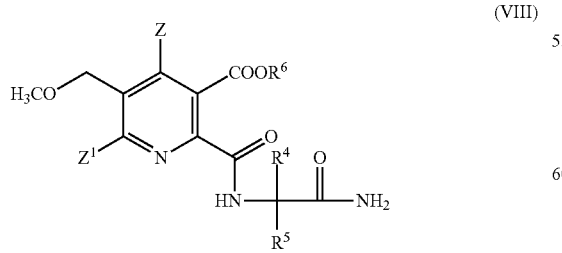
(VIII)

where the symbols are as in formula (III), and
(ii-3) condensation of amide (VIII) to yield the herbicidal imidazolinone (III).

Steps (ii-2) and (ii-3) may be carried out as a one-pot reaction.

In one embodiment step (ii-2) is carried out in analogy to the procedure disclosed in example 10 of EP-A 0 322 616. Compound (I), a substituted 2-aminoalkane carboxamide (VI) and a tertiary amine, preferably triethylamine are reacted in a polar aprotic solvent, such as acetonitrile, to yield an ammonium salt (VIII), which can be acidified to an acid (VIII).

Alternative procedures are disclosed in U.S. Pat. No. 4,518,780 and EP-A 0 144 595. In the latter document the addition of a nitrogen base selected from pyridine, the picolines, quinoline and lutidine is disclosed to improve the regioselectivity of the reaction, i.e. to increase the amount of 2-addition product.

In one embodiment of step (ii-3) amido compound (VIII), preferably in the form of an ammonium salt (R$^6$ is HNR$_3$), is reacted with an alkali metal methoxide, preferably NaOCH$_3$ in methanol in analogy to example 11 of EP 0 322 616. The resulting suspension is held at reflux until complete conversion. After cooling the mixture is acidified to obtain compound (III) either as the ammonium salt (acidification to a pH of about 4) or the free acid (acidification to pH ≤2).

In a further preferred embodiment, the reaction mixture from step (ii-2) is reacted with methanol (generally 2 to 100 equivalents based on (VIII)) in the presence of an aqueous base (generally 3 to 100 equivalents based on (VIII)), the base being preferably selected from MOH and MOCH$_3$, where M is an alkali metal, preferably Na or K, particularly Na.

The reaction is carried out at a temperature in the range of from 20 to 120° C., preferably 40 to 90° C. The reaction can be carried out at atmospheric pressure or at elevated pressure, preferably the pressure forming at the desired reaction temperature. The reaction time is generally from 1 to 8 h, preferably from 1 to 5 h.

Isolation of product (III) can be achieved by standard methods. In a preferred embodiment water is added and organic solvents are distilled off. The residue can be taken up in water and acidified, whereupon compound (III) precipitates. After filtration the crude product can be further purified, e.g. by stirring with water or recrystallization.

In a further embodiment compound (III) is prepared by
(i) preparation of a compound (I), where Y is OH, as outlined above;
(ii-1) conversion of compound (I) to the anhydride (VI),

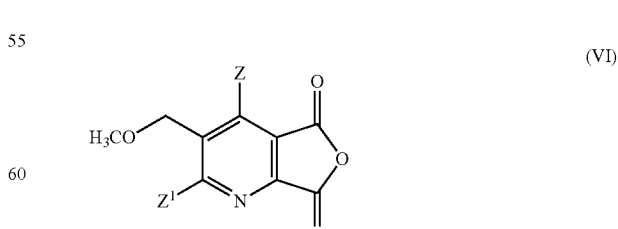
(VI)

(ii-2) reacting anhydride (VI) with aminocarbonitrile (IX),

H$_2$N—CR$^4$R$^5$—CN (IX)

where $R^4$ and $R^5$ are as in formula (III), to obtain amidonitrile compound (X),

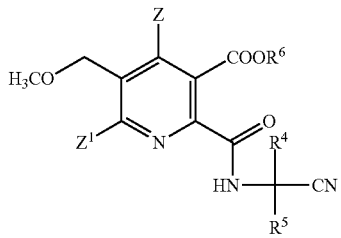

where $R^4$, $R^5$ and $R^6$ are as in formula (III),
(ii-3) hydrolysis of the nitrile group in compound (X) to yield amide (VIII),

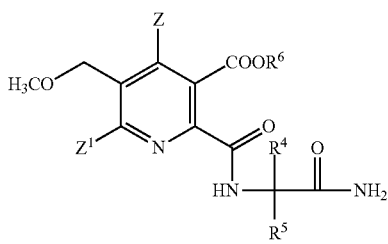

where the symbols have the same meaning as in formula (III) and
(ii-4) condensing amide (VIII) to yield the herbicidal imidazolinone (III).

Preparation of the anhydride (VI) can be carried out as described above.

Aminocarbonitriles (IX), which are employed in step (ii-2), are commercially available or can be prepared by methods known in the art. Generally 0.8 to 1.2 equivalents aminonitrile (IX) per equivalent of compound (VI) are used, preferably 0.95 to 1.1.

The reaction is carried out in a solvent, which is preferably selected from aromatic hydrocarbons, preferably toluene, mesitylenes, chlorinated aromatic hydrocarbons, such as chlorobenzene, dichlorobenzene, chlorinated hydrocarbons, such as 1.2-dichloroethane, dichloromethane, acetic acid, and mixtures thereof.

If acetic acid is not used as the main solvent, addition of 0.5 to 4 equivalents, preferably 1 to 3 equivalents (based on compound (I)), is advantageous. Further advantageous additives that improve the selectivity of the ring-opening reaction (2 versus 3 position) are listed in EP-A 0 144 555, and comprise pyridine, 4-picoline, 2-picoline and quinoline.

The reaction is generally carried out at a temperature range of from about 40 to about 120° C., preferably of from about 60 to about 100° C. The reaction time is generally from about 1 to about 3 h.

In a preferred embodiment anhydride (VI) is dissolved in the solvent and brought to the reaction temperature, and aminonitrile (IX) is gradually added. After completion of the reaction and cooling, nitrile compound (X) can be isolated by standard methods.

In a preferred embodiment, however, compound (X) is not isolated but the reaction mixture is directly used in the following hydrolyzation step of the nitrile (step iv-3)

In a typical procedure a slight excess (e.g. 1.1 to 1.5 equivalents based on (X)) of a strong mineral acid, preferably sulfuric acid (preferably in a concentration of 30 to 98%) and water (e.g. 2 to 10 equivalents) are added at a temperature which is generally in the range of about 30 to 120° C., preferably 50 to 90° C. The mixture is further stirred until complete conversion. The reaction time is generally from 1 to 8 h, preferably 1 to 5 h.

Workup and isolation can be achieved by standard methods, such as an aqueous solution (e.g. as its ammonium salt). In a preferred embodiment the reaction mixture is directly used in the following condensation step (ii-4).

In an alternative embodiment hydrolysis of the nitrile group is effected by reaction with aqueous $NaOH/H_2O_2$ as disclosed, e.g. in EP-A 0 144 595 and U.S. Pat No. 4,518,780.

Condensation of amido compound (VIII) to the herbicidal imidazolinone may be carried out as described above.

All of the above processes are particularly preferred for the preparation of the compound of formula (III) where Z and $Z^1$ are H, $R^6$ is H, $R^4$ is $CH_3$ and $R_5$ is $CH(CH_3)_2$, i.e. imazamox.

The invention is illustrated by the following examples without limiting it thereby.

EXAMPLES

Comparative Example 1

Preparation of 5-(methoxymethyl)-2,3-pyridinedicarboxylic acid (according to ex. 3 of EP-A 0 548 532)

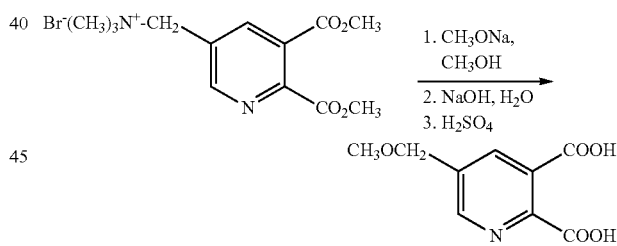

A mixture of 25% sodium methoxide in methanol (270 g, 1.25 mol) and [(5,6-dicarboxy-3-pyridyl)-methyl]trimethylammonium bromide, dimethyl ester (Ia) (347 g, 1.00 mol) in methanol (650 ml) is heated at reflux for 1 hour under nitrogen. Water (1 l) and sodium hydroxide (80.0 g, 2.0 mol) are added and the reaction mixture is distilled until the pot is 100-105° C. The reaction mixture is cooled to room temperature, treated with sulfuric acid to adjust the pH to a value from 1.5 to 2 and filtered to obtain a solid. The solid is washed with water and dried in a vacuum oven to obtain the title product as a white solid (mp 161-162° C.) which is greater than 99% pure by HPLC analysis.

No water is present in the first step of the reaction (methoxylation of the 5-methyl group), which requires a laborious drying or solid isolation process for the starting material. Thus the process is less suitable for industrial application.

Comparative Example 2

Preparation of disodium 5-(methoxymethyl)pyridine-2,3-dicarboxylate from disodium [5,6-(dicarboxylate-3-pyridyl)methyl]trimethylammonium bromide (according to ex. 3 of EP-A 0 747 360)

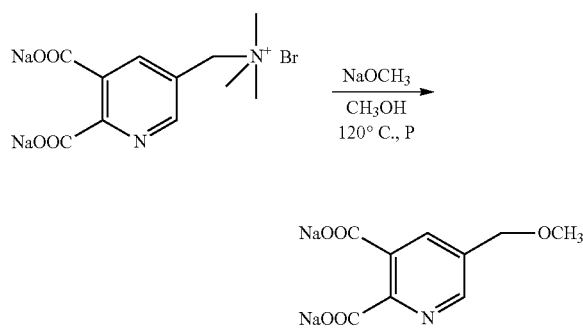

A mixture of disodium [(5,6-dicarboxylate-3-pyridyl)nethyl]trimethylammonium bromide (5.0 g, 13.8 mmol) and a 25% wt/wt solution of sodium methoxide in methanol (4.46 g, 20.7 mmol of $NaOCH_3$) in 75 g of methanol is heated at 120° C. for 21 hours in a pressure reactor. The reaction is cooled to room temperature, treated with water and con-centrated to a final weight of 55.03 g. A 5.0 g sample is assayed by LC analysis (30% $CH_3CN$, 0.77 M $H_3PO_4$). The remainder of the reaction solution is evaporated to dryness to give a solid residue, identified by NMR analysis.

In spite of the higher temperature the reaction time is considerably longer than in the inventive process.

Example 1

Preparation of 5-(methoxymethyl)-2,3-pyridinedicarboxylic acid

Bromide (IIa), (0.41 mol) containing about 40% by weight of water, is taken up in methanol. Aqueous NaOH is added over 30 min. at 35° C., and the mixture is stirred for an additional 15 min. $NaOCH_3$ in methanol is added over 20 min at 45° C.

The reaction mixture is moved to a Parr pressure reactor and heated to the reaction temperature (80 to 100° C.). At about 60° C. the reactor is closed, whereupon pressure builds up reaching about 40 to 45 Psi at the reaction temperature. No external pressure is applied.

After 6 to 8 h, the mixture is cooled and work up is conducted according to known procedures.

E.g. the reaction mixture is cooled to room temperature, treated with sulfuric acid to adjust the pH to a value from 1.5 to 2 and filtered to obtain a solid. The solid is washed with water and dried in a vacuum oven to obtain the title product as a white solid (mp 161 to 162° C.) which is greater than 99% pure by HPLC analysis.

In a similar fashion examples 2 to 17 shown in Table 1 were carried out.

TABLE 1

| ex. | temperature [° C.] | pressure [bar] | % $H_2O$ after addition of NaOH | molar ratio NaOMe | molar ratio NaOH | weight ratio MeOH | reaction-time [h] | conversion [%] |
|---|---|---|---|---|---|---|---|---|
| 2 | 100 | 2.76-3.45 | 48 | 3 | 0 | 3 | 8.75 | 99.6 |
| 3 | 100 | 2.76-3.45 | 42 | 5 | 0 | 3 | 8 | 98.4 |
| 4 | 100 | 2.76-3.45 | 61 | 5 | 0 | 3 | 8 | 95.2 |
| 5 | 90 | 1.38-2.07 | 48 | 5 | 0 | 5 | 8 | 91.9 |
| 6 | 80 | 1.03-1.38 | 48 | 5 | 0 | 3 | 8 | 81.8 |
| 7 | 100 | 2.76-3.45 | 55 | 2 | 3 | 5 | 8 | 87.5 |
| 8 | 100 | 2.76-3.45 | 56 | 1 | 4 | 5 | 8 | 92.4 |
| 9 | 100 | 2.76-3.45 | 43 | 1.5 | 4 | 5 | 8 | 99.7 |
| 10 | 100 | 2.76-3.45 | 43 | 2 | 4 | 5 | 8 | 100 |
| 11 | 100 | 2.76-3.45 | 51 | 1.5 | 3 | 5 | 8 | 100 |
| 12* | 100 | 2.76-3.45 | 50 | 2 | 2.5 | 5 | 8 | 99.5 |
| 13* | 100 | 2.76-3.45 | 51 | 1.5 | 1 | 6 | 8 | 80.0 |
| 14 | 100 | 2.76-3.45 | 42 | 1.5 | 3 | 3 | 5.5 | 85.0 |
| 15 | 100 | 2.76-3.45 | 40 | 1.5 | 3 | 3 | 6.75 | 94.0 |
| 16 | 100 | 2.76-3.45 | 40 | 1.5 | 3 | 3 | 8 | 99.8 |
| 17 | 100 | 2.76-3.45 | 37 | 1.5 | 3 | 2 | 8 | 99.9 |

*NaOH added to (II) before $H_2O$ removal under vacuum. MeOH added, then stripped (II), split in 2. NaOMe added just before Parr high temp/press run.

It can be seen that higher temperatures and longer reaction times improve the conversion rate. In addition, conversion is enhanced by a higher amount of base. The process of the invention can be carried out in the presence of large amounts of water as compared to the Comparative Examples.

Example 18

Synthesis of [(5,6-dicarboxy-3-pyridyl)methyl] trimethylammonium bromide, dimethylether (IIa)

a) Synthesis of dimethyl 5-(bromomethyl)-2,3-pyridinedicarboxylate (Va) (50% conversion)

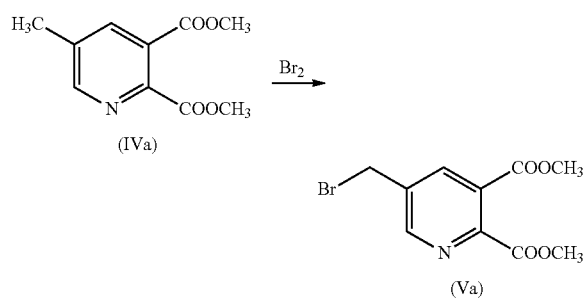

218.4 g (1.0 mol) compound (Va) were dissolved in 1139.0 g 1,2-dichloroethane (EDC) and 160.0 g water were charged and heated to 72° C. (about 1-2° C. below reflux). 14.4 g (0.075 mol) 2,2'-azobis(2-methylbutyronitrile) (Vazo 67) in 160.0 g EDC were added over 2 h at 72° C. After 30 minutes 143.8 g (0.9 mol) bromine were added over 2 h, under pH control (pH 5-7) by dosage of about 375.0 g aqueous NaOH (15%). The mixture was stirred over 1 h for reaction completion (HPLC assay). After cooling to 40° C. the phases were separated.

b) Synthesis of Compound (IIa)

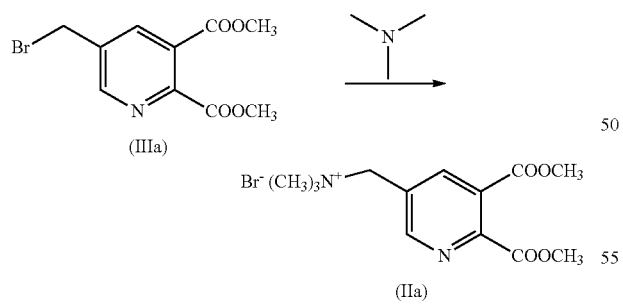

288.1 g (1.0 mol) compound (IIIa) in mixture with di- and tribromination byproducts in 3359.0 g EDC (organic phase from step a, including unreacted compound (IIa) and higher brominated byproducts) were charged. The mixture was heated to 30° C. and the vessel evacuated to 200 mbar.

70.9 g (1.2 mol) trimethylamine (TMA) was added to the gas phase during 2 h at 40° C. (closed system). The mixture was stirred one additional hour (HPLC con-version check: compound (IIIa) in solution <0.1%).

Excess TMA was distilled off together with EDC (mass: 40% of the EDC mass) transferred to step 2 (1344 g) at 50-55° C. (370-250 mbar). The pH of the distillate was <9. 630.0 g water was sprayed to the wall so that the solid is dissolved and the mixture was transferred to the next vessel. The mixture was then stirred 0.25 h, and the lower organic phase was separated at 40° C. 320.4 g EDC were added. The mixture was stirred and the lower organic phase was separated at 40° C. The back extraction was repeated (40° C.) with 320.4 g EDC. The two organic back extraction phases were combined with the first organic phase and re-cycled to the next bromination batch (after addition of 50% fresh compound (IIa) for a further cycle.

Steps a) and b) were repeated six times. In the last cycle no compound (IVa) was added in step a) and 0.8 mol TMA were added in step b).

The overall conversion rate of compound (IIa) is 96.6%. The yield of compound (IIa) (over 7 cycles) is 77.4% at a purity of >95% (as determined by HPLC).

The invention claimed is:

1. A process for manufacturing a compound of formula (I),

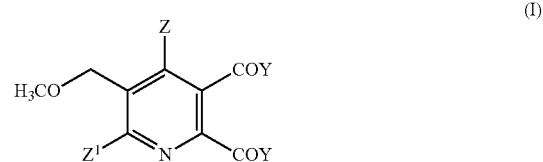

wherein
Z is H or halogen;
$Z^1$ is H, halogen, CN or $NO_2$;
Y is OM, and
M is an alkali metal or an alkaline earth metal, the process comprising
(i) reacting and methoxylating under pressure in a closed vessel at a temperature of from about 90° C. to 105° C. a compound of formula (II)

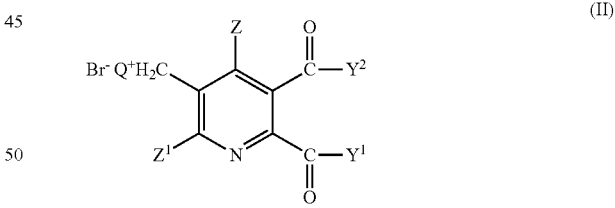

in a reaction mixture comprising methanol, water, a base, and the compound of formula (II), thereby forming the compound of formula (I);
wherein
Q is a tertiary aliphatic or cyclic, saturated, partially unsaturated or aromatic amine;
Z is H or halogen;
$Z^1$ is H, halogen, CN or $NO_2$;
$Y^1$ and $Y^2$ are each independently $OR^1$, $NR^1R^2$, or when taken together $Y^1Y^2$ is —O—, —S— or —$NR^3$—;
$R^1$ and $R^2$ are each independently H, $C_1$-$C_4$ alkyl optionally substituted with $C_1$-$C_4$ alkoxy, or phenyl optionally substituted with one to three $C_1$-$C_4$ alkyl groups, $C_1$-$C_4$ alkoxy groups, or halogen atoms, or phenyl optionally substituted with one to three $C_1$-$C_4$ alkyl groups, $C_1$-$C_4$ alkoxy groups or halogen atoms;

$R^3$ is H or $C_1$-$C_4$ alkyl;

the water is present in the reaction mixture in the range of 30 to 70% by weight, based on the sum of the water and the compound of formula (II) in the reaction mixture;

the base comprises MOH and optionally $MOCH_3$, where M is an alkali metal or an alkaline earth metal;

the molar ratio of total amount of the base added to the compound of formula (II) in the reaction mixture is 3-7:1;

the weight ratio of the methanol to the compound of formula (II) in the reaction mixture is in the range of from 1-10:1;

the molar ratio of $MOCH_3$, if present, added to the compound of formula (II) in the reaction mixture is in the range of 1.25-7:1;

the molar ratio of MOH added to the compound of formula (II) in the reaction mixture is in the range of 1-5:1; and the reaction time is in the range of from 6 to 20 h.

2. The process of claim 1, further comprising:

(i-1) reacting a compound of formula (IV),

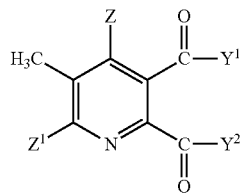

(IV)

with bromine in the presence of a radical initiator in a solvent mixture comprising an aqueous phase and an organic phase, wherein the organic phase comprises a solvent selected from the group consisting of 1,2-dichloroethane, chlorobenzene, 1,2-dichlorobenzene, 1,3-dichlorobenzene, 1,4-dichlorobenzene and tetrachloromethane, and where the pH-value of the aqueous phase is from 3 to <8, to obtain a compound of formula (V),

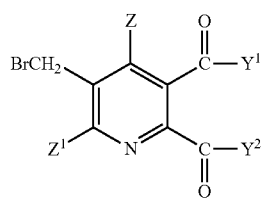

(V)

and (i-2) reacting the compound of formula (V) with a tertiary amine Q in a solvent at a temperature range of 0 to 100° C. to the compound of formula (II).

3. The process of claim 1, wherein the compound of formula (II) is the compound (IIa)

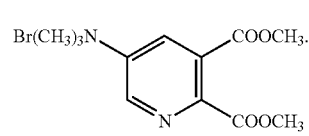

(IIa)

4. The process of claim 1, wherein the base comprises $MOCH_3$ and MOH.

5. The process of claim 4 wherein the molar ratio of $MOCH_3$ to the compound of formula (II) is in the range of from 1.25-2:1.

6. The process of claim 1, wherein the reaction temperature is in the range of from about 90 to 100° C.

7. The process of claim 1, which is carried out at a pressure of 1.01 to 5.00 bar.

8. The process of claim 1, wherein, prior to reacting and methoxylating under pressure in the closed vessel at the temperature of from about 90° C. to 105° C., the process further comprises:

adding an aqueous MOH base to a mixture comprising the compound of formula (II), water, and methanol, thereby forming the reaction mixture.

9. The process of claim 1, wherein, prior to reacting and methoxylating under pressure in the closed vessel at the temperature of from about 90° C. to 105° C., the process further comprises:

adding an aqueous MOH base to a mixture comprising the compound of formula (II), water, and methanol; and adding an $MOCH_3$ base in methanol to the mixture to which the aqueous MOH base has been added, thereby forming the reaction mixture.

10. The process of claim 9, comprising:

adding the aqueous MOH base at a temperature in a range from about 25° C. to 40° C.; and adding the $MOCH_3$ base in methanol at a temperature in a range from about 40° C. to 50° C.

11. The process of claim 10, wherein:

the MOH base is NaOH; and the $MOCH_3$ base is $NaOCH_3$.

12. A process for preparing a compound of formula (III),

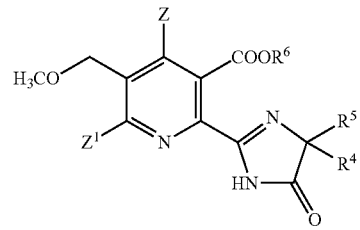

(III)

wherein

Z is H or halogen;

$Z^1$ is H, halogen, CN or $NO_2$;

$R^4$ is $C_1$-$C_4$ alkyl;

$R^5$ is $C_1$-$C_4$ alkyl, $C_3$-$C_6$ cycloalkyl or $R^4$ and $R^5$, when taken together with the atom to which they are attached, represent a $C_3$-$C_6$ cycloalkyl group optionally substituted with methyl, and $R^6$ is hydrogen; a group of the formula —N=C (lower alkyl)$_2$; $C_1$-$C_{12}$ alkyl optionally substituted with one of the following groups: $C_1$-$C_3$ alkoxy, halogen, hydroxyl, $C_3$-$C_6$-cycloalkyl, benzyloxy, furyl, phenyl, halophenyl, lower alkylphenyl, lower alkoxyphenyl, nitrophenyl, carboxyl, lower alkoxycarbonyl, cyano or tri lower alkylammonium; $C_3$-$C_{12}$ alkenyl optionally substituted with one of the following groups:
$C_1$-$C_3$ alkoxy, phenyl, halogen or lower alkoxycarbonyl or with two $C_1$-$C_3$ alkoxy groups or two halogen groups; $C_3$-$C_6$ cycloalkyl optionally substituted with one or two $C_1$-$C_3$ alkyl groups; or
a cation;
comprising:
(i) preparing the compound of formula (I) according to claim 1;
(ii) converting the compound of formula (I) into the compound of formula (III).
13. The process of claim 12, further comprising:
(i) preparing the compound (I), where Y is OH,
(ii-1) converting the compound (I) to the compound of formula (VI),

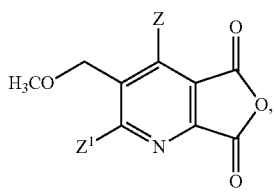
(VI)

wherein
Z is H or halogen;
$Z^1$ is H, halogen, CN or $NO_2$;
(ii-2) reacting the compound of formula (VI) with a compound of formula (VII), $H_2N$—$CR^4R^5$—$CONH_2$ (VII),
wherein
$R^4$ is $C_1$-$C_4$ alkyl;
$R^5$ is $C_1$-$C_4$ alkyl, $C_3$-$C_6$ cycloalkyl or $R^4$ and $R^5$, when taken together with the atom to which they are attached, represent a $C_3$-$C_6$ cycloalkyl group optionally substituted with methyl,
to yield a compound of formula (VIII),

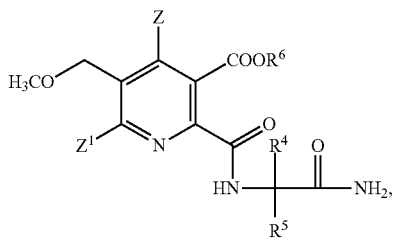
(VIII)

and
(ii-3) condensing the compound of formula (VIII) to yield the compound of formula (III).
14. The process of claim 12, further comprising:
(i) preparing the compound (I), where Y is OH,
(ii-1) converting the compound of formula (I) to the compound of formula (VI),

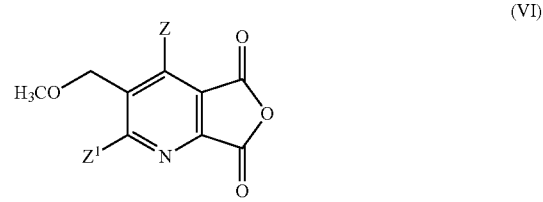
(VI)

(ii-2) reacting the compound of formula (VI) with a compound of formula (IX),
$H_2N$—$CR^4R^5$—$CN$ (IX);
to obtain a compound of formula (X),

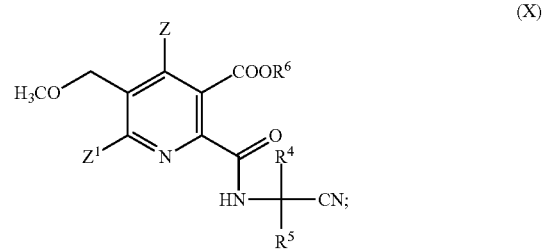
(X)

(ii-3) hydrolyzing the compound of formula (X) to yield a compound of formula (VIII),

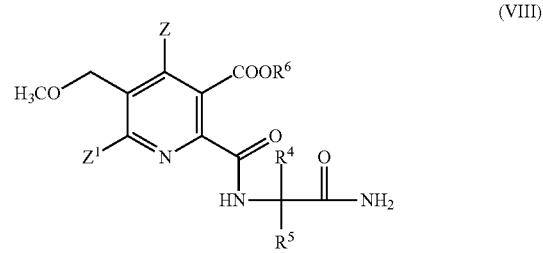
(VIII)

and
(ii-4) condensing the compound of formula (VIII) to yield the compound of formula (III).

* * * * *